United States Patent [19]

Gross

[11] Patent Number: 4,716,107

[45] Date of Patent: Dec. 29, 1987

[54] METHOD FOR DIAGNOSIS OF A.I.D.S.

[76] Inventor: Robert L. Gross, 15 Vasquez Ave., San Francisco, Calif. 94127

[21] Appl. No.: 941,531

[22] Filed: Dec. 10, 1986

Related U.S. Application Data

[63] Continuation of Ser. No. 584,658, Feb. 29, 1984, abandoned.

[51] Int. Cl.[4] .............. G01N 33/567; G01N 33/555; G01N 33/564; C12Q 1/02
[52] U.S. Cl. ......................................... 435/7; 435/2; 435/4; 435/5; 435/29; 435/30; 436/501; 436/503; 436/506; 436/510; 436/519; 436/520; 436/811
[58] Field of Search ................. 435/2, 4, 5, 7, 29, 435/30; 436/501, 503, 506, 510, 518, 519, 520, 536, 537, 543, 528, 533, 534, 63, 811

[56] References Cited

U.S. PATENT DOCUMENTS

| | | | |
|---|---|---|---|
| 3,988,115 | 10/1976 | Modabber | 436/534 |
| 3,999,944 | 12/1976 | Grosser et al. | 436/519 |
| 4,426,446 | 1/1984 | Thomson | 436/519 |
| 4,436,824 | 3/1984 | Bishop | 436/529 |
| 4,455,379 | 6/1984 | Bekesi | 436/504 |
| 4,511,662 | 4/1985 | Baran et al. | 436/534 |
| 4,520,113 | 5/1985 | Gallo et al. | 436/504 |

OTHER PUBLICATIONS

Morbidity and Mortality Weekly Report, Center for Disease Control, Atlanta, Georgia, (May 21, 1982), vol. 31, No. 19.
Morbidity and Mortality Weekly Report, vol. 31, No. 37, pp. 507–514 (Sep. 24, 1982).
Fauci, A. S. et al, Annals of Internal Medicine, vol. 100, pp. 92–106 (1984), NIH Conference—Jun. 23, 1983.
Dong, J. et al, Federation Proceedings, American Societies for Experimental Biology, 42(4):951, Abstract 3853 (1983).
"Abnormal Spontaneous Rosette Formation and Rosette Inhibition in Lung Carcinoma", Robert L. Gross et al., *New England Journal of Medicine*, 292:439–443, Feb. 27, 1975.
In Vitro Immunological Studies on East African Cancer Patients . . . ", Robert L. Gross et al., Int. J. Cancer, 15, 132–138, (1975).
"Spontaneous Rosette and Rosette-Inhibition Tests on Fresh and Cryopreserved Lymphocytes", R. L. Gross et al, *Cryobiology*, 12, 455–462, (1975).
"Immunologic Assessment of Patients with Pulmonary Metaplasia and Neoplasia", Robert L. Gross et al., presented at 1978 Symposium on Environmental Carcinogens.

*Primary Examiner*—Margaret Moskowitz
*Attorney, Agent, or Firm*—Townsend & Townsend

[57] ABSTRACT

A novel method for the diagnosis of Acquired Immune Deficiency Syndrome (A.I.D.S.) is disclosed, involving the use of immunocytoadherence (rosette inhibition) techniques. The method is based on the discovery that the lymphocytes of A.I.D.S. patients are unusually resistant to antithymocyte serum, and that the plasma of A.I.D.S. patients is capable of conferring this resistance to normal lymphocytes. Accordingly, the diagnostic method involves performing rosette inhibition tests on the patient's lymphocytes or on lymphocytes from a healthy donor after treatment with the patient's plasma. Any observable lessening of inhibition in comparison with a control is related to the presence of A.I.D.S.

12 Claims, No Drawings

METHOD FOR DIAGNOSIS OF A.I.D.S.

This is a continuation of application Ser. No. 584,658 filed Feb. 29, 1984, now abandoned.

The present invention relates to immunological assays for diagnostic purposes. In particular, this invention relates to the diagnosis of A.I.D.S. by the use of immunological techniques.

BACKGROUND OF THE INVENTION

One of the most alarming occurrences in recent years is the proliferation of Acquired Immune Deficiency Syndrome (commonly referred to as "A.I.D.S."). The number of undiagnosed cases per year has escalated rapidly and a large number of deaths has resulted. In spite of the mounting concern, the origin and cure of the syndrome have eluded the medical and scientific community.

Certain diagnostic techniques for A.I.D.S. are known, each having serious shortcomings which limit its effectiveness. One such technique is a helper-suppresser cell assay performed on T-cells and T-cell subpopulations, where the reversal of the helper-suppresser ratio is taken as a indication of the presence of A.I.D.S. This assay is seriously lacking in specificity and sensitivity. Another technique involves a determination of the thymosin level, the elevation of the level being an indication of the presence of A.I.D.S. Unfortunately, this technique gives positive results only when the disease has reached an advanced stage, and even then it fails to give consistently positive readings in all cases where A.I.D.S. is known to be present.

SUMMARY OF THE INVENTION

It has now been discovered that immunocytoadherence tests (commonly known as rosette tests), and in particular, rosette inhibition tests, provide an effective method for A.I.D.S. diagnosis, permitting effective diagnosis of this syndrome in its early stages with reliable results. Specifically, it has been discovered that the T-lymphocytes of A.I.D.S. patients are unusually resistant to antibodies or antisera which bind T-cells, a phenomenon which is directly observable in rosette inhibition tests. It has further been discovered that the plasma of A.I.D.S. patients confers this resistance to normal T-lymphocytes in a manner which is also directly observable in rosette inhibition tests. The present invention therefore provides a diagnostic method for A.I.D.S. whereby rosette inhibition tests are performed on a subject's lymphocytes or on lymphocytes from a healthy donor which had been treated with the subject's plasma. According to the test procedure, any lessening of inhibition in comparison with a control test (and thus conveniently referred to as "inhibition of inhibition") is related to the presence of A.I.D.S. The term "plasma" herein is intended to include unclotted plasma as well as plasma which has been allowed to clot (i.e., serum).

DESCRIPTION OF THE PREFERRED EMBODIMENTS

When rosette inhibition tests are performed on A.I.D.S. lymphocytes, the high resistance of these lymphocytes to antibodies or antisera which bind T-cells appears in the test results as a lessened ability of the antibodies or serum to inhibit the rosette formation. As in rosette inhibition tests in general, monoclonal or polyclonal antibodies with the appropriate specificity can be used. Antithymocyte serum (ATS), however, is preferred. Thus, when A.I.D.S. is present, the percentage of rosette forming cells among those treated with ATS is higher, falling somewhere between the percent which would occur in healthy cells incubated with ATS (lower limit) and that which would occur on healthy cells with no ATS present (upper limit).

Since the plasma of an A.I.D.S. subject confers this resistance to normal T-lymphocyte cells, the preferred assay technique is one where normal lymphocytes incubated in the patient's plasma are tested rather than the patient's own lymphocytes. This technique permits one to use the same lymphocyte source for both the variable and control tests, thereby providing a direct comparison for determining the inhibition of inhibition.

According to this embodiment, healthy lymphocytes are obtained from a normal donor, and plasma is obtained from the subject under study, by conventional methods. The lymphocytes are then suspended in the plasma and the suspension is incubated for a sufficient period of time (typically on the order of 30 minutes) for the transfer of characteristics to occur. The cell concentration in the suspension is not critical and can vary widely. A suitable concentration will be one which permits a reasonably accurate calculation in the cell counting steps described below. In general, a cell concentration ranging from about $1 \times 10^6$ to about $1 \times 10^7$ cells/ml will provide the best results.

Rosette inhibition tests are then conducted according to conventional procedures, using an antiserum having affinity toward the lymphocytes, and sheep erythrocytes capable of forming rosettes with the lymphocytes. Examples of such procedures are described in Gross, et al., "Abnormal Spontaneous Rosette Formation and Rosette Inhibition in Lung Carcinoma," *New England Journal of Medicine*, 292:439–443 (1975); Gross, et al., "In Vitro Immunological Studies on East African Cancer Patients. II. Increased sensitivity of blood lymphocytes from untreated Burkitt Lymphoma patients to inhibition of spontaneous rosette formation," *International Journal of Cancer*, 15:132–138 (1975); and Gross, et al., "Spontaneous Rosette and Rosette-Inhibition Tests on Fresh and Cryopreserved Lymphocytes," *Cryobiology*, 12:455–462 (1975). The disclosures of these publications are incorporated herein by reference.

Rather than using a range of antiserum dilutions as disclosed in these publications, however, a single dilution is used. The actual dilution is not critical, but rather is selected to provide a percent inhibition within a range which is convenient to measure and which will demonstrate a high degree of response to the resistance effect of A.I.D.S. plasma. In general, dilutions within the range of about 1:10 to about 1:200, preferably from about 1:20 to about 1:80, will provide the best results. The sheep erythrocyte concentration is similarly variable, and in most cases will fall between about 1.0% and about 5.0%.

Once the rosettes are formed, the percentage of rosette forming cells based on the total number of lymphocytes in the sample is determined by conventional rosette counting techniques. Examples of such techniques are described in Brain, et al., "Rosette Formation by Peripheral Lymphocytes. II. Inhibition of the Phenomenon," *Clinical and Experimental Immunology*, 8:441–449 (1971); and Wybran, et al., "Thymus-derived Rosette-Forming Cells in Various Human Disease States: Cancer, Lymphoma, Bacterial and Viral Infections and Other Diseases," *Journal of Clinical Investiga-*

*tion*, 52:1026–1032 (1973). The disclosures of these publications are also incorporated herein by reference. Preferably a minimum of 200 lymphocytes is counted per sample.

The percent rosette inhibition is then calculated by comparing the percent rosette-forming cells obtained with the antiserum to that obtained without the antiserum. The latter is obtained by substituting an inert suspending medium for the antiserum. Examples of such calculations are found in the Gross et al. articles cited above. The inhibition of inhibition is then determined by comparing the inhibition figure for the plasma test with the inhibition figure for a parallel test conducted by substituting an inert suspending medium for the plasma. Commercially available materials may be used as the suspending media for these control tests.

The following examples are offered for illustrative purposes, and are intended neither to define nor limit the invention in any manner.

EXAMPLE

Lymphocytes from a healthy donor are obtained as follows. A 20 ml heparinized blood sample is obtained in a sterile Vacutainer tube. A White Blood Cell count and a differential are determined on the sample by conventional techniques. The sample is then centrifuged for ten minutes at 1200 rpm, and the plasma is decanted off. The cell pellet is then resuspended to its original volume in RPMI 1640 culture medium (Microbiological Associates, Bethesda, Md.). A 6 ml portion of the suspension is then layered over 4 ml of a density gradient centrifugation medium. Commercially available media include LSM (Litton Bionetics, Kensington, Md.) and Lymphoprep (Pharmacia Fine Chemicals, Inc., New Market, N.J.). Alternatively, a medium may be prepared fresh to a specific gravity of 1.077. Centrifugation is continued for about thirty minutes at 1200 rpm (400×g). The resulting mononuclear cell layer at the gradient/supernatant interface is then aspirated with a Pasteur pipette into a 50 ml sterile centrifuge tube. The cells are washed twice with 30–40 ml of Hanks balanced salt solution (HBSS) and resuspended in media consisting of RPMI 1640 culture medium with 10% fetal calf serum, L-glutamine and antibiotics to a cell concentration of about $5 \times 10^6$ cells/ml.

Plasma from a subject to be tested for A.I.D.S. is then obtained by centrifuging a 10–15 ml sample of heparinized blood. A 100-microliter aliquot of this plasma is combined with a 100-microliter aliquot of the lymphocyte suspension, and the resulting suspension is incubated at room temperature for thirty minutes, then centrifuged for ten minutes at 1200 rpm. After two washings in HBSS, the cells are resuspended in 100 microliters of media (RPMI 1640 with 10% fetal calf serum and L-glutamine), and 100 microliters of antithymocyte serum (ATS) at a dilution of 1:50 are added. An example of a useful ATS preparation is ATGAM (Upjohn Co., Kalamazoo, Mich.), a horse polyclonal antihuman thymocyte serum.

Control tubes are prepared simultaneously. A control tube for normal rosette formation is prepared by combining 100 microliters of the normal lymphocyte suspension with 100 microliters of HBSS. A control tube for normal rosette inhibition is prepared by combining 100 microliters of the normal lymphocyte suspension with 100 microliters of the 1:50 ATS dilution. All tubes are incubated at room temperature for thirty minutes.

Then, to each tube are added 100 microliters of fetal calf serum and 100 microliters of 2.5% sheep red blood cells (SRBC). The tubes are centrifuged for ten minutes at 1200 rpm and incubated at room temperature for two hours, then gently resuspended for counting. The percentage of rosette-forming lymphocytes out of the total number of lymphocytes present is then determined by counting according to known techniques, notably the method of Brain et al. and Wybran et al., referenced above.

Rosette inhibition due to ATS is calculated for both the normal lymphocytes and the lymphocytes incubated with the subject's plasma. A comparison of these two inhibition figures provides the extent of inhibition of rosette inhibition resulting from the presence of the A.I.D.S. plasma. A lowering in the degree of inhibition indicates the presence of A.I.D.S. A convenient formula for calculating the inhibition of rosette inhibition is as follows:

$$\% \text{ Inhibition of Inhibition} = \frac{\% \ RFC_{subj, \ ATS} - \% \ RFC_{ATS}}{\% \ RFC_{normal} - \% \ RFC_{ATS}}$$

where

"% RFC": % rosette-forming cells based on total lymphocytes

"subj, ATS": treated with both subject's plasma and ATS

"ATS": treated with ATS only

"normal": treated with neither subject's plasma nor ATS.

The procedure described above was applied to 39 human male subjects of whom 8 were controls (6 healthy sexually active homosexuals and 2 healthy non-homosexuals), 21 were suspect of having A.I.D.S. but undiagnosed (having either lymphadenopathy, recurrent infections, or a high-risk life style), and 10 known A.I.D.S. patients. The latter were recently diagnosed yet not on treatment at the time of testing, and were further specifically diagnosed as having Kaposi's sarcoma, pneumocystis or both.

The results were as follows, providing a persuasive correlation between "Percent Inhibition of Inhibition" and A.I.D.S.:

| GROUP | SUBJECT NO. | % INHIBITION OF INHIBITION | |
|---|---|---|---|
| CONTROL | 1 | 0 | Mean: 2.8% |
|  | 2 | 2 | Range: 0–8% |
|  | 3 | 7 |  |
|  | 4 | 0 |  |
|  | 5 | 0 |  |
|  | 6 | 5 |  |
|  | 7 | 8 |  |
|  | 8 | 0 |  |
| SUSPECT AIDS | 9 | 51 | Mean: 25.3% |
|  | 10 | 82 | Range: 0–82% |
|  | 11 | 22 |  |
|  | 12 | 9 |  |
|  | 13 | 20 |  |
|  | 14 | 7 |  |
|  | 15 | 20 |  |
|  | 16 | 21 |  |
|  | 17 | 5 |  |
|  | 18 | 56 |  |
|  | 19 | 23 |  |
|  | 20 | 82 |  |
|  | 21 | 10 |  |
|  | 22 | 28 |  |
|  | 23 | 8 |  |
|  | 24 | 33 |  |

-continued

| GROUP | SUBJECT NO. | % INHIBITION OF INHIBITION | |
|---|---|---|---|
| | 25 | 5 | |
| | 26 | 30 | |
| | 27 | 5 | |
| | 28 | 15 | |
| | 29 | 0 | |
| KNOWN AIDS | 30 | 87 | Mean: 56.3% |
| | 31 | 100 | Range: 31–100% |
| | 32 | 31 | |
| | 33 | 67 | |
| | 34 | 70 | |
| | 35 | 35 | |
| | 36 | 35 | |
| | 37 | 65 | |
| | 38 | 38 | |
| | 39 | 35 | |

The foregoing description is offered primarily for purposes of illustration. The invention as a whole is not intended to be limited to the particular features or procedural steps described. Various modifications and substitutions will be readily apparent to those skilled in the art which still fall within the scope of the invention as claimed hereinafter.

What is claimed is:

1. A method for the diagnosis of acquired immune deficiency syndrome in a human subject, comprising:
   (a) combining (1) a member selected from the group consisting of lymphocytes obtained from said human subject's blood and lymphocytes obtained from the blood of a healthy donor and incubated with plasma obtained from said human subject's blood with (2) antiserum which specifically binds to T-lymphocytes, to form a suspension;
   (b) combining said suspension with erythrocytes capable of rosette formation with said T-lymphocytes;
   (c) comparing the level of rosette formation in said suspension with the level of rosette formation resulting from the combination of healthy donor lymphocytes with said erythrocytes in the absence of said antiserum and without treatment with said subject's plasma, to obtain a value representing the percent inhibition of rosette formation attributable to said antiserum; and
   (d) comparing the value obtained in step (c) with a control value representing the percent inhibition of rosette formation resulting from the addition of anti-T-lymphocyte antiserum to a T-lymphocyte sample from a healthy donor combined with said erythrocytes to detect any variation occurring between said values which is attributable to said subject's lymphocytes or plasma, as an indication of the presence of acquired immune deficiency syndrome in said subject.

2. A method as in claim 1, wherein the control value used in step (d) is obtained by combining lymphocytes from the healthy donor with an inert suspending medium and antiserum which specifically binds to T-lymphocytes, further combining erythrocytes with the combination of lymphocytes and antiserum, and comparing the level of rosette formation in a combination of lymphocytes from the healthy donor with the erythrocytes.

3. A method for the diagnosis of acquired immune deficiency syndrome in a human subject, comprising:
   (a) isolating plasma from a sample of said human subject's blood;
   (b) suspending in said plasma a predetermined amount of lymphocytes from a healthy donor;
   (c) incubating said suspension with antiserum which specifically binds to T-lymphocytes at a dilution and in an amount selected to inhibit binding of T-lymphocytes in the suspension to sheep red blood cells;
   (d) combining said treated suspension with a predetermined quantity of erythrocytes capable of rosette formation with said lymphocytes;
   (e) comparing the level of rosette formation in said suspension with a non-inhibiting control level obtained by combining the T-lymphocytes of the healthy donor with an inert suspending medium and said antiserum, further combining said T-lymphocytes, inert suspending medium, and antiserum with erythrocytes capable of rosette formation, and determining the level of rosette formation, to obtain a value representing the percent inhibition of rosette formation attributable to said antiserum; and
   (f) comparing the value obtained in step (e) with a control value representing the percent inhibition of rosette formation resulting from the addition of anti-T-lymphocyte antiserum to a T-lymphocyte sample from a healthy donor combined with said erythrocytes, to detect any variation occurring in said value which is attributable to said plasma, as an indication of the presence of acquired immune deficiency syndrome in said subject.

4. A method as in claim 3, wherein the control value of step (f) is obtained by combining the T-lymphocytes of the healthy donor with an inert suspending medium and said antiserum, further combining the T-lymphocytes, inert suspending medium, and antiserum with erythrocytes capable of rosette formation, and comparing the level of rosette formation with a non-inhibition control level to provide said control value.

5. A method according to claim 3 in which said lymphocytes are human lymphocytes and said antiserum is horse antihuman thymocyte serum.

6. A method according to claim 3 in which said lymphocytes are human lymphocytes and said erythrocytes are sheep red blood cells.

7. A method according to claim 3 in which the dilution of step (c) is from about 1:10 to about 1:200.

8. A method according to claim 3 in which the dilution of step (c) is from about 1:20 to about 1:80.

9. A method according to claim 3 in which step (e) is performed by observing at least about two hundred lymphocytes per determination.

10. A method according to claim 3 in which the lymphocytes of step (b) prior to suspension in said plasma are in the form of a cell suspension in fluid media at a concentration of from about $1 \times 10^6$ to about $1 \times 10^7$ cells/ml.

11. A method for the diagnosis of acquired immune deficiency syndrome in a human subject, comprising:
   (a) isolating plasma from a sample of said human subject's blood;
   (b) combining a predetermined amount of said plasma with a suspension containing a predetermined amount of lymphocytes from a healthy human donor at a cell concentration of from about $1 \times 10^6$ to about $1 \times 10^7$ cells/ml;

(c) incubating the suspension resulting from step (b) with a predetermined amount of antithymocyte serum which specifically binds to T-lymphocytes at a dilution of from about 1:20 to about 1:80;

(d) combining said incubated suspension with a suspension of a predetermined quantity of sheep red blood cells at a concentration ranging from about 1.0% to about 5.0%;

(e) comparing the level of rosette formation in the suspension resulting from step (d) with a non-inhibition level obtained by combining the T-lymphocytes of the healthy donor with an inert suspending medium and said antiserum, further combining the T-lymphocytes, inert suspending medium, and antiserum with erythrocytes capable of rosette formation, and determining the level of rosette formation, to obtain a value representing the percent inhibition of rosette formation attributable to said antiserum; and (f) comparing the value obtained in step (e) with a control value representing the percent inhibition of rosette formation resulting from the addition of anti-T-lymphocyte antiserum to a T-lymphocyte sample from a healthy donor combined with said erythrocytes, to detect any variation occurring in said value which is attributable to said plasma, as an indication of the presence of acquired immune deficiency syndrome in said subject.

12. A method as in claim 11, wherein the control value of step (f) is obtained by combining the T-lymphocytes of the healthy donor with an inert suspending medium and said antiserum, further combining the T-lymphocytes, inert suspending medium, and antiserum with erythrocytes capable of rosette formation, and comparing the level of rosette formation with a non-inhibition control level to provide said control value.

* * * * *